US007745112B1

(12) United States Patent
Walton et al.

(10) Patent No.: US 7,745,112 B1
(45) Date of Patent: Jun. 29, 2010

(54) GENETIC INDICATORS OF TOBACCO CONSUMPTION

(75) Inventors: Robert Walton, Oxford (GB); Eoin McKinney, Oxford (GB); Sara Marshall, Oxford (GB); Michael Murphy, Oxford (GB); Kenneth Welsh, Oxford (GB)

(73) Assignee: g-Nostics Limited (GB)

( * ) Notice: Subject to any disclaimer, the term of this patent is extended or adjusted under 35 U.S.C. 154(b) by 856 days.

(21) Appl. No.: 10/130,907

(22) PCT Filed: Nov. 24, 2000

(86) PCT No.: PCT/GB00/04476

§ 371 (c)(1),
(2), (4) Date: Nov. 12, 2002

(87) PCT Pub. No.: WO01/38567

PCT Pub. Date: May 31, 2001

(30) Foreign Application Priority Data

Nov. 24, 1999 (GB) ................................. 9927806.1

(51) Int. Cl.
*C12Q 1/70* (2006.01)
*C12P 19/34* (2006.01)
(52) U.S. Cl. .......................... 435/6; 435/91.1; 435/91.2
(58) Field of Classification Search ........................ None
See application file for complete search history.

(56) References Cited

U.S. PATENT DOCUMENTS

| 5,500,343 | A | 3/1996 | Blum et al. | |
|---|---|---|---|---|
| 5,783,680 | A | 7/1998 | Brunner et al. | |
| 2001/0051344 | A1* | 12/2001 | Shalon et al. | 435/6 |

FOREIGN PATENT DOCUMENTS

| WO | WO 98/48785 | 11/1998 |
|---|---|---|
| WO | WO 99/27919 | 6/1999 |
| WO | WO 01/38567 | 5/2001 |

OTHER PUBLICATIONS

Rossing et al. "Genetic Influences on Smoking: Candidate Genes" Environmental Health Perspectives, May 1998, vol. 106, pp. 231-238.*
Lucentini, J. "Gene Association Studies Typically Wrong" The Scientist, 2004, vol. 20, p. 20.*
Kroese et al. "Genetic tests and their evaluation: Can we answer the key questions?"Genetics in Medicine, Nov./Dec. 2004, vol. 6, No. 6, pp. 475-480.*
Kobayashi et al. "Human dopamine hydroxylase gene: two mRNA types having difference 3'-terminal regions are produced through alternative polyadneylation", Nucleic Acid Research, 1989, vol. 17, pp. 1089-1102.*
Johnstone et al. "Genetic Variation in Dopaminergic Pathways and Short term effectiveness of the Nicotine Patch", Pharmacogenomics, 2004, 14:83-90.*
Johnstone et al. "Polymorphisms in dopamine metabolic enzymes and tobacco consumption in smokers: seekign confirmation of the association in a follow-up study", Pharmacogenomics, 2002, 12:585-587.*
GenBank accession No. X13264.*
GenBank Accession No. X13260.*
Ionnidis Plost Med, 2005, 2(8):e124.*
Hattersley et al. Lancet, 2005, vol. 366, pp. 1315-1323.*
Kim et al. Am. J. of Med. Genetics, 2002, 108:140-147.*
Hegele, Arterioscler. Thromb. Vasc. Biol. 2002, 22:1058-1061.*
Bell et al., The New Genetics in Clinical Practice, British Journal of Medicine, 316(Feb. 14): 618-20, 1998.
Benowitz et al., Drug therapy. Pharmacologic aspects of cigarette smoking and nicotine addition, New England Journal of Medicine, 319: 1318-30, 1988.
Blum et al., Dopamine D2 Receptor Gene Variants: Association and Linkage Studies in Impulsive-addictive-compulsive Behaviour, Pharmacogenetics, 5(3): 121-41, 1995.
Boustead et al., CYP2D6 Genotype and Smoking Behaviour in Cigarette Smokers, Pharmacogenetics, 7(5): 411-4, 1997.
Bunce et al., Molecular HLA Typing the Brave New World, Transplantation, 64(11): 1505-13, 1997.
Bunce et al., Phototyping: Comprehensive DNA Typing for HLA-A, B, C, DRB1, DRB3, DRB4, DRB5, DQB1 by PCR with 144 Primer Mixes Utilizing Sequence-specific Primers (PCR-SSP), Tissue Antigens, 46(5): 355-67, 1995.
Callum et al., The UK Smoking Epidemic, London, Health Education Authority, 1998.
Caporaso et al., The Genetics of Smoking: The Dopamine Receptor Transporter (DAT) Polymorphisms in a Smoking Cessation Study (abstract), Proceedings of the American Association for Cancer Research, 38: 168-9, 1997.
Cholerton et al., Poor Metabolisers of Nicotine and CYP2D6 Polymorphism, Lancet, 343(8888): 62-3, 1994.
Clarke et al., Tobacco Smoking, Genes and Dopamine, Lancet, 352(9122): 84-5, 1998.
Comings et al., Studies of the Potential Role of the Dopamine D1 Receptor Gene in Addictive Behaviours, Molecular Psychiatry, 2(1): 44-56, 1997.
Comings et al., The Dopamine D2 Receptor (DRD2) Gene: A Genetic Risk Factor in Smoking, Pharmacogenetics, 6(1): 73-9, 1996.
Cubells et al., Dopamine Beta-hydroxylase: Two Polymorphisms in Linkage Disequilibrium at the Structural Gene DBH Associate with Biochemical Phenotypic Variation, Human Genetics, 102: 533-540, 1998.
Faraj et al., Platelet Monoamine Oxidase Activity in Alcoholics, Alcoholics with Drug Dependence, and Cocaine Addicts, Alcohol Clinical and Experimental Research, 18(5): 1114-20, 1994.

(Continued)

*Primary Examiner*—Sarae Bausch
(74) *Attorney, Agent, or Firm*—Wolf, Greenfield & Sacks, P.C.

(57) ABSTRACT

There are disclosed genetic screens for predicting the likely extent of tobacco consumption in human subjects based on screening for the presence or absence of genetic variants shown to be associated with tobacco consumption in smokers.

8 Claims, No Drawings

OTHER PUBLICATIONS

Fowler et al., Neuropharmacological Actions of Cigarette Smoke: Brain Monoamine Oxidase B(MAO B) Inhibition, Journal of Addictive Diseases, 17(1): 23-34, 1998.

Gabel et al., Homovanillic Acid and Dopamine-beta-hydroxylase in Male Youth; Relationships with Paternal Substance Abuse and Antisocial Behaviour, American Journal of Drug and Alcohol Abuse, 21(3): 363-78, 1995.

Garcia-Closas et al., Association between CYP1A1 Polymorphism and Smoking in a Control Population: Implications for the Study of Genetic Factors on Cancer Risk, Proceedings for the American Association for Cancer Research, 38(Mar.): 211, 1997.

Heath et al., Personality and the Inheritance of Smoking Behaviour: A Genetic Perspective, Behavioral Genetics, 25(2): 103-17, 1995.

Heath et al., Genetic Contribution to Risk of Smoking Initiation; Comparisons Across Birth Cohorts and Across Cultures, Journal of Substance Abuse, 5(3): 221-46, 1993.

Hurt et al., A Comparison of Sustained-release Bupropion and Placebo for Smoking Cessation, New England Journal of Medicine, 337(17): 1195-202, 1997.

Imperial Cancer Research Fund, General Practice Research Group, Effectiveness of a Nicotine Patch in Helping People Stop Smoking: Results of a Randomised Trail in General Practice, British Medical Journal, 306(6888): 1304-8, 1993.

Imperial Cancer Research Fund, Oxcheck Study Group, Effectiveness of Health Checks Conducted by Nurses in Primary Care: Final Results of the Oxcheck Study, British Medical Journal, 310(6987): 1099-104, 1995.

Jorenby et al., A Controlled Trial of Sustained-release Bupropion, a Nicotine Patch, or Both for Smoking Cessation, New England Journal of Medicine, 340(9): 685-91, 1999.

Lerman et al., Lack of Association of Tyrosine Hydroxylase Genetic Polymorphism with Cigarette Smoking, Pharmacogenetics, 7(6): 521-4, 1997.

Lerman et al., Evidence Suggesting the Role of Specific Genetic Factors in Cigarette Smoking, Health Psychology, 18(1): 14-20, 1999.

MacKay et al., Tobacco and the Developing World, British Medical Bulletin, 52(1): 206-21, 1996.

McKinney et al., Association Between Polymorphisms in Dopamine Metabolic Enzymes and Tobacco Consumption in Smokers, Pharmacogenetics, 10(6): 483-91, 2000.

Noble et al., D2 Dopamine Receptor Gene and Cigarette Smoking: A Reward Gene?, Medical Hypotheses, 42(4): 257-60, 1994.

Pastinen et al., Minisequencing: a specific tool for DNA analysis and diagnostics on oligonucleotide arrays, Genome Research, 7: 606-14, 1997.

Pianezza et al., Nicotine Metabolism Defect Reduces Smoking, Nature, 393: 750, 1998.

Roskey et al., DNA sequencing by delayed extraction-matrix-assisted laser desorption/ionization time of flight mass spectrometry, Proceedings of the National Academy of Science USA, 93: 4724-9, 1996.

Rossing et al., Genetic Influences on Smoking: Candidate Genes, Environmental Health Perspectives, 106(5): 231-8, 1998.

Sabol et al., A Genetic Association for Cigarette Smoking Behaviour, Health Psychology, 18(1): 7-13, 1999.

Schafer et al., DNA variation and the future of human genetics, Nature Biotechnology, 16: 33-9, 1998.

Schneider et al., Efficacy of a Nicotine Nasal Spray in Smoking Cessation: A Placebo-controlled Double-blind Trial, Addiction, 90(12): 1671-82, 1995.

Sellers et al., Pharmacogenetics and Ethnoracial Differences in Smoking, Journal of the American Medical Association, 280(2): 179-80, 1998.

Shields et al., Dopamine D4 Receptors and the Risk of Cigarette Smoking in African-Americans and Caucasians, Cancer Epidemiology, Biomarkers, and Prevention, 7(6): 453-8, 1998.

Shumaker et al., Mutation detection by solid phase primer extension, Human Mutations, 7: 346-54, 1996.

True et al., Genetic and Environmental Contributions to Smoking, Addiction, 92(10): 1277-87, 1997.

Underhill et al., A pre-Columbian Y chromosome-specific transition and its implications for human evolutionary history, Proceedings of the National Academy of Science USA, 93: 196-200, 1996.

Vandenberg et al., High-activity Catechol-O-methyltransferase Allele is More Prevalent in Polysubstance Abusers, American Journal of Medical Genetics, 74(4): 439-42, 1997.

Van Der Sande et al., Nationwide Prevalence Study of Hypertension and Related Non-communicable Diseases in The Gambia, Tropical Medicine and International Health, 2(11): 1039-48, 1997.

Wicklegreen, I. Teaching the Brain to Take Drugs, Science, 280(Jun. 26): 2045-7, 1998.

AF050737. *Homo sapiens* dopamine D2 receptor (DRD2) gene, complete cds. Apr. 4, 2001.

GENBANK Submission; NIH/NCBI, Accession No. NM_00787 gi: 4503260; Kobayashi et al.; Oct. 31, 2000. 3 pages.

GENBANK Submission; NIH/NCBI, Accession No. NM_00787 gi: 18426905; Barkley et al.; Aug. 20, 2006. 7 pages.

GENBANK Submission; NIH/NCBI, Accession No. NM_00787 gi: 116534899; Kollins et al.; Dec. 21, 2008. 5 pages.

OMIM Database Entry. Accession No. 126450. Dopamine receptor D2; DRD2. 15 pages, printed Jan. 2010.

SNP Database Accession No. rs1800497. 1 page, printed Jan. 2010.

Houhou et al., Expression of human dopamine beta-hydroxylase in mammalian cells infected by recombinant vaccinia virus. Mechanisms for membrane attachment. J Biol Chem. May 26, 1995; 270(21): 12601-6.

Imperial Cancer Research Fund, Oxcheck Study Group. Effectiveness of health checks conducted by nurses in primary care results of the Oxcheck study after one year. Br J Med. BMJ. Jan. 29, 1994;308:308-12.

Lamouroux et al., The primary structure of human dopamine-beta-hydroxylase: insights into the relationship between the soluble and the membrane-bound forms of the enzyme. EMBO J. Dec. 20, 1987;6(13):3931-7.

Sabol et al., A functional polymorphism in the monoamine oxidase A gene promoter. Hum Genet. Sep. 1998;103(3):273-9.

Fiore, MC, et al., Treating Tobacco Use and Dependence. Clinical Practice Guideline. Rockville, MD: U.S. Department of Health and Human Services. Public Health Service, Jun. 2000, AHCPR Supported Clinical Practice Guidelines: Treating Tobacco Use and Dependence (revised 2000). Health Services/Technology Assessment Test:, Chapter 6.

Grandy, D.K. et al., The human dopamine D2 receptor gene is located on chromosome 11 at q22-q23 and identifies a TaqI RFLP. Am J Hum Genet. Nov. 1989;45(5):778-85.

Hauge, X.Y. et al., Detection and characterization of additional DNA polymorphisms in the dopamine D2 receptor gene. Genomics. Jul. 1991;10(3):527-30.

Henningfield, J.E. Nicotine medications for smoking cessation. N Engl J Med. Nov. 2, 1995;333(18):1196-203. Review.

Neville, M.J. et al., Identification and characterization of ANKK1: a novel kinase gene closely linked to DRD2 on chromosome band 11q23.1. Hum Mutat. Jun. 2004;23(6):540-5.

Silagy, C. et al., Nicotine replacement therapy for smoking cessation. Cochrane Database Syst Rev. 1-106. 2007.

West, R. et al., Smoking cessation guidelines for health professionals: an update. Health Education Authority. Thorax. Dec. 2000;55(12):987-99.

\* cited by examiner

GENETIC INDICATORS OF TOBACCO CONSUMPTION

RELATED APPLICATIONS

This application is a national stage filing 35 U.S.C. §120 or 35 U.S.C. §365(c) of PCT International application PCT/GB00/04476 (entitled "Genetic Indicators of Tobacco Consumption", in the name of Isis Innovation Limited) designating the United States of America, and filed Nov. 24, 2000, of which this application is a national stage filing under 35 U.S.C. §371, which was published under PCT Article 21(2) in English.

The present invention is concerned with novel associations between known polymorphisms in the dopamine β-hydroxylase and monoamine oxidase A genes and tobacco consumption in smokers.

Smoking is one of the most important public health issues facing health professionals and governments. In the United Kingdom alone there are 120,000 deaths attributed to tobacco use each year (Callum, 1998). Effective therapy is available for tobacco dependence but cessation rates of about 20% are the best that can currently be achieved (ICRF, 1993; Schneider, 1995). Deeper understanding of the molecular basis for tobacco addiction could lead to more effective strategies for prevention and for helping people to stop smoking.

Twin studies show a major genetic component to tobacco addiction (Heath, 1995). Recent mathematical models of data from 3997 twin pairs show that starting to smoke and continuing with the habit both have a substantial genetic component (True, 1997). In this study, genetic factors accounted for 50% of the variance in risk of smoking initiation and 70% of the risk of persistent smoking. Taking up smoking and continuing with the habit are likely to come under separate genetic influences (Heath, 1993).

There is substantial evidence to suggest that dopaminergic neurones arising in the ventral tegmental area of the thalamus and projecting to the nucleus accumbens are the final common pathway for addiction to a wide variety of substances (Clarke, 1998; Wickelgreen, 1998). Enzymes involved in dopamine metabolism may therefore be important in determining susceptibility to substance abuse. Monoamine oxidase is involved in the oxidative deamination of dopamine and noradrenaline. Levels of this enzyme are lower in platelets of patients with substance abuse (Faraj, 1994) and smokers have lower monoamine oxidase activity in the brain than non-smokers (Fowler, 1998). It has been suggested that the inhibitors of monoamine oxidase present in tobacco smoke contribute to the development of addiction (Fowler, 1998). Similarly, lower levels of dopamine β-hydroxylase are related to drug dependence (Gabel, 1995), although no link has as yet been established with smoking. Patients with high activities of catechol O-methyl transferase are more susceptible to developing polysubstance abuse (Vandenbergh, 1997), but again there is no known association with smoking.

Relatively few studies have examined the effects of genetic variation (i.e. polymorphisms) on the amount of tobacco consumed by smokers. However in a study of the dopamine D1 receptor Dde I restriction fragment length polymorphism in 238 smokers, those with the 11 genotype were more likely to smoke more than 40 cigarettes a day than those with 1,2 or 22 genotypes (Comings, 1997). In one study on the dopamine D2 receptor Taq IA polymorphism there was no significant difference in numbers of cigarettes smoked between those homozygous or heterozygous for the A1 allele, but another study suggested that the A1 allele was commoner in those who smoked more heavily (Comings, 1996). A study on 72 African Americans found a trend for people with the longer alleles of the dopamine D4 receptor variable number tandem repeat polymorphism to smoke fewer cigarettes a day. The mean(SD) was 18(9) cigarettes in those with more than 6 repeat sequences and 13(6) in those with 7 or more repeats. In this small study the effects were not significant and the association was not reproduced in a larger group of Caucasians (n=403).

Associations have also been shown between cytochrome P450 enzymes and tobacco consumption. A study on 263 Caucasians showed that people with one CYP1A1 Msp 1 variant allele smoked 23(22) pack years whilst controls smoked 33(29) pack years (Garcia-Closas, 1997). The CYP1A1 gene contributes to aryl hydrocarbon hydroxylase activity. This enzyme activates carcinogenic polyaromatic hydrocarbons and has been studied in smokers because of its relationship to the development of lung cancer. The mechanism by which it may exert an effect on tobacco consumption is unknown. Studies on the cytochrome P450 enzyme CYP2D6, which may be important in nicotine metabolism (Cholerton, 1994), have shown no difference in tobacco consumption between extensive and poor metabolisers (Boustead, 1997). However a study on CYP2A6 showed that people with one or more variant alleles smoked a mean(SD) 18.4 (6.0) cigarettes a day compared to 22.7(13.6) in those homozygous for the common allele (n=161) (Pianezza, 1998).

The present inventors have investigated the relationship between common polymorphisms in enzymes involved in dopamine metabolism and age at initiation of smoking and current cigarette consumption and concluded that individuals with one or more dopamine β-hydroxylase 1368 A alleles smoked more cigarettes than those with the GG genotype (adjusted mean difference 3.3, p=0.009), whilst individuals with a monoamine oxidase A 1460 C allele smoked fewer cigarettes than those homozygous for T (−3.2, p=0.007). Thus, dopamine β-hydroxylase 1368 and monoamine oxidase A 1460 genotypes predict whether a person is a heavy smoker and how many cigarettes they consume. The results of this investigation support the view that these enzymes determine a smoker's requirement for nicotine and may explain why certain people are predisposed to develop tobacco addiction and why some find it very difficult to stop smoking. This finding has important implications for smoking prevention and offers potential for developing patient-specific therapy for smoking cessation.

In a first aspect, the invention provides a method for predicting the likely extent of tobacco consumption in a human subject, which method comprises screening for the presence or absence in the genome of the human subject of the monoamine oxidase A 1460 C allele and/or the monoamine oxidase A 1460 T allele, wherein the presence of at least one monoamine oxidase A 1460 C allele indicates that the subject is less likely to be a heavy smoker than subjects who are homozygous for the monoamine oxidase A 1460 T allele.

The invention further provides a method for predicting the likely extent of tobacco consumption in a human subject, which method comprises screening for the presence or absence in the genome of the human subject of the dopamine β-hydroxylase 1368 A allele and/or the dopamine β-hydroxylase 1368 G allele, wherein the presence of at least one dopamine β-hydroxylase 1368 A allele indicates that the subject is more likely to be a heavy smoker than subjects who are homozygous for the dopamine β-hydroxylase 1368 G allele.

The present inventors were the first to provide evidence linking genetic variation in dopamine metabolic enzymes to tobacco consumption. It seems likely that the enzymes in question exert their effects on smoking behaviour by altering dopamine breakdown, however it is also possible that they have more wide ranging effects since they form key parts of the metabolic pathways of other monoamines.

The human monoamine oxidase A gene may also be denoted herein by the abbreviation 'MAO A'; the human dopamine β-hydroxylase gene may also be denoted herein by the abbreviation 'DBH'.

The novel associations described herein are consistent with the suggestion that dopaminergic reward pathways are important in determining tobacco consumption. Polymorphisms that reduce dopamine activity may contribute to a 'reward deficiency syndrome' where self administration of nicotine restores dopaminergic transmission to 'normal' levels (Blum, 1995). If this is so one would expect to find that the polymorphisms included in the study described herein were either themselves responsible for increased dopamine breakdown and impaired dopaminergic transmission or in linkage disequilibrium with genetic variants which have this effect.

In a second aspect, the invention provides a method for predicting the response of a human subject to a treatment designed to assist smoking cessation, which method comprises screening for the presence or absence in the genome of the human subject of the monoamine oxidase A 1460 C allele and/or the monoamine oxidase A 1460 T allele.

In this aspect, the invention further provides a method for predicting the response of a human subject to a treatment designed to assist smoking cessation, which method comprises screening for the presence or absence in the genome of the human subject of the dopamine β-hydroxylase 1368 A allele and/or the dopamine β-hydroxylase 1368 G allele.

In essence, the methods of this second aspect of the invention provide rapid diagnostic genomic tests for smokers which could be used to help in identifying which smoking cessation aid/treatment is most likely to be effective in that individual.

A deeper understanding of why people smoke may be the key to developing more effective ways of helping them to stop. The genetic component to smoking behaviour is likely to be multifactorial with different molecular mechanisms contributing to the habit in different people. In general terms, identification of the mechanisms involved in causing disease may allow specific treatments to be used. By way of an example, one person with heart failure may have hypertensive cardiomyopathy, another mitral incompetence—both may benefit from diuretics but specific treatments aimed at modifying the underlying pathophysiology may be more appropriate.

At present in the United Kingdom nicotine replacement therapy is suggested for all people wishing to give up smoking. Other effective treatments are likely to become available soon (Hurt, 1997; Jorenby, 1999). It may be that different patients will respond to different treatments. For example, people who metabolise nicotine quickly may respond best to a nicotine patch. Those who metabolise nicotine very rapidly may need a higher replacement dose than slower metabolisers. People with polymorphisms in the dopamine transporter may respond particularly well (or badly) to dopamine reuptake inhibitors for smoking cessation. Using genotyping to target the most appropriate treatment to the individual smoker could make treatments for tobacco addiction more effective.

The presence of a monoamine oxidase A 1460 C allele in the genome of an individual might indicate reduced monoamine oxidase activity, leading to impaired dopaminergic transmission. Smoking would be a means of restoring dopaminergic function to normal. Such individuals might experience reduced desire to smoke if their dopamine levels were increased by using a dopamine reuptake inhibitor such as buprorion, whereas individuals with 'normal' dopamine function might respond best to behavioural therapy. Accordingly, genetic screens for the presence or absence of at least one MAO A 1460 C allele could possibly be used to target treatment with dopamine reuptake inhibitors to those who are most likely to benefit from such treatment.

The polymorphisms in the dopamine β-hydroxylase gene that were included in the study described herein have not previously been linked to smoking phenotype or to human disease. The 910 polymorphism causes an amino acid substitution in the protein (ala 304 ser) but the 1368 variant is 'silent'. Associations have been found however between serum dopamine β-hydroxylase levels and two polymorphisms in linkage disequilibrium with each other and close to the 910 and 1368 loci, namely DBH*444 g/a and DBH STR (Cubells, 1998). It seems highly likely therefore that the DBH gene is a major determinant of dopamine β-hydroxylase activity and it may be that the polymorphisms studied by the present inventors are in linkage disequilibrium with an allele that controls this activity.

Accordingly, the invention also provides a method for predicting the likely extent of tobacco consumption in a human subject, which method comprises screening for the presence or absence in the genome of the human subject of one or more alleles in close physical proximity to or in linkage disequilibrium with the dopamine β-hydroxylase 1368 A allele and a method for predicting the response of a human subject to a treatment designed to assist smoking cessation, which method comprises screening for the presence or absence in the genome of the human subject of one or more alleles in close physical proximity to or in linkage disequilibrium with the dopamine β-hydroxylase 1368 A allele. In both methods, the said allele is preferably selected from the group consisting of DBH*444 g, DBH*444 a and an allele of the DBH STR polymorphism (Cubells, 1998).

Both polymorphisms in the monoamine oxidase A gene included in the study described herein (positions 941 and 1460) are conservative substitutions and are unlikely to be themselves responsible for variations in phenotype. Again it seems likely that these alleles are in linkage disequilibrium with alleles that cause functional changes in monoamine oxidase activity. The invention thus provides a method for predicting the likely extent of tobacco consumption in a human subject, which method comprises screening for the presence or absence in the genome of the human subject of one or more alleles in close physical proximity to or in linkage disequilibrium with the monoamine oxidase A 1460 C allele and a method for predicting the response of a human subject to a treatment designed to assist smoking cessation, which method comprises screening for the presence or absence in the genome of the human subject of one or more alleles in close physical proximity to or in linkage disequilibrium with the monoamine oxidase A 1460 C allele.

In both of the above methods, the allele in close physical proximity to the MAO A C allele is preferably a variable number tandem repeat in the promoter region of the gene (Sabol, 1998), most preferable MAO A uVNTR allele 1 or MAO A uVNTR allele 4. This variable number tandem repeat polymorphism is in linkage disequilibrium with a number of genetic markers in the monoamine oxidase A and monoamine oxidase B genes. Alleles with 3.5 or four copies of the repeat sequence are transcribed between two and 10 times more efficiently than those with three or five copies of the repeat. It is very likely that this increased transcription results in increased enzyme activity.

As would be readily apparent to persons skilled in the art of human genetics, "linkage disequilibrium" occurs between a marker polymorphism (e.g. a DNA polymorphism which is 'silent') and a functional polymorphism (i.e. genetic variation which affects phenotype or which contributes to a genetically determined trait) if the marker is situated in close proximity to the functional polymorphism. Due to the close physical proximity, many generations may be required for alleles of the marker polymorphism and the functional polymorphism to be separated by recombination. As a result they will be present together on the same haplotype at higher frequency than expected, even in very distantly related people. As used herein the term "close physical proximity" means that the two markers/alleles in question are close enough for linkage disequilibrium to be likely to arise.

As mentioned previously, the genetic component to smoking behaviour is likely to be multifactorial with different molecular mechanisms contributing to the habit in different people. The dopamine metabolic genes analysed in this study are likely to form only part of the genetic component of nicotine addiction (Rossing, 1998). Polymorphisms in dopamine receptors D1 (Comings, 1997) and D2 (Comings, 1996; Noble, 1994) are likely to contribute, although not all studies confirm these associations (Lerman, 1999; Sabol, 1999). The gene for the D4 receptor has a variable number tandem repeat polymorphism in which the 7 repeat allele reduces the affinity of the receptor for dopamine. This polymorphism seems to predispose to smoking only in African Americans in whom it is more frequent (40%) than in Caucasians (22%) (Shields, 1998).

Another important protein is the dopamine transporter (DAT 1) which is responsible for removing dopamine from the synaptic cleft and thereby terminating its action. A variable number tandem repeat occurs in the 3' untranslated region of this gene. The 9 repeat allele, of uncertain functional significance, is associated with a reduced likelihood of being a smoker (Lerman, 1999). Smokers who have this allele start smoking later and have longer periods of abstinence than those with fewer repeat sequences. The effects of the dopamine receptor and transporter polymorphisms on smoking may be mediated by an association with a novelty seeking personality (Lerman, 1999).

In view of the foregoing, it is within the scope of the invention to performs screens for the presence or absence in the genome of the human subject of at least one allele selected from the group consisting of: dopamine β-hydroxylase 1368 A, dopamine β-hydroxylase 1368 G, monoamine oxidase A 1460 C and monoamine oxidase 1460 T in conjunction with screens (in the same human subject) for other polymorphisms associated with smoking behaviour, for example as part of a panel of screens. In a preferred embodiment, the panel of screens would include up to 10 different polymorphisms.

The individual screens to be included in the panel may be selected from the group consisting of: screens for DBH 1368 A and/or one or more alleles in close physical proximity to or in linkage disequilibrium with DBH 1368 A, screens for MAO A 1460 C and/or one or more alleles in close physical proximity to or in linkage disequilibrium with MAO A 1460 C, screens for one or more alleles of the dopamine D1 receptor DdeI RFLP (Comings, 1997) or one or more alleles in linkage disequilibrium therewith, screens for one or more alleles of the dopamine D2 receptor TaqI RFLP (Comings, 1996; Noble, 1994) or one or more alleles in linkage disequilibrium therewith, screens for one or more alleles of the dopamine D4 receptor VNTR polymorphism (Shields, 1998) or one or more alleles in linkage disequilibrium therewith, screens for one or more alleles of the VNTR in the 3' UTR of the DAT 1 gene (Caporaso, 1997; Lerman, 1999) or one or more alleles in linkage disequilibrium therewith, screens for one or more alleles of the CYP1A1 MspI RFLP or one or more alleles in linkage disequilibrium therewith and screens for one or more variant alleles of CYP2A6, CYP2D6, the tyrosine hydroxylase gene (TH) or the 5-hydroxytryptamine transporter gene (5-HTT).

The step of screening for the presence or absence of specific polymorphic alleles, also referred to herein as 'genotyping', can be carried out using any of the methodologies known in the art.

In a preferred embodiment, genotyping of single nucleotide polymorphisms (SNPs) is carried out by performing PCR using allele specific primers, a technique known in the art as PCR-SSP (Bunce, 1995). Further techniques are known in the art for the scoring of SNPs (see review by Schafer, A. J. and Hawkins, J. R. in Nature Biotechnology, Vol 16, pp33-39 (1998), including mass spectrometry, particularly matrix-assisted laser desorption/ionization time-of-flight mass spectrometry (MALDI-TOF-MS, see Roskey, M. T. et al., 1996, PNAS USA, 93: 4724-4729), single nucleotide primer extension (Shumaker, J. M. et al., 1996, Hum. Mutat., 7: 346-354; Pastinen, T. et al., 1997, Genome Res., 7: 606-614) and DNA microchips/microarrays (Underhill, P. A. et al., 1996, PNAS USA, 93: 196-200). The known techniques for scoring polymorphisms are of general applicability and it would therefore be readily apparent to persons skilled in the art that the known techniques could be adapted for the scoring of single nucleotide polymorphisms in the monoamine oxidase A gene and the dopamine β-hydroxylase gene.

Variable number tandem repeat polymorphisms, such as the MAO A uVNTR, can be scored by performing non-allele-specific PCR using primers corresponding to sequences on either side of the variable number repeat region. Different alleles will give rise to PCR products of slightly different sizes which may be resolved by gel electrophoresis or other techniques known in the art.

Restriction fragment length polymorphisms are typically scored by digesting genomic DNA with the appropriate enzyme then performing a Southern blot using a labelled probe corresponding to the polymorphic region (see Molecular Cloning: A Laboratory Manual, Sambrook, Fritsch and Maniatis, Cold Spring Harbor Laboratory, Cold Spring Harbor, N.Y.).

In a still further aspect, the invention provides a kit for use screening for the presence or absence of at least one allele of the dopamine β-hydroxylase 1368 A/G polymorphism and at least one allele of the monoamine oxidase 1460 C/T polymorphism, the kit comprising at least an oligonucleotide comprising 10 or more contiguous nucleotides from the dopamine β-hydroxylase gene, including the polymorphic locus at position 1368 and an oligonucleotide comprising 10 or more contiguous nucleotides from the monoamine oxidase A gene, including the polymorphic locus at position 1460.

The oligonucleotide molecules for inclusion into the kit are preferably from 10 to 50 nucleotides in length, even more preferably from 20-30 nucleotides in length, and may be DNA, RNA or a synthetic nucleic acid, and may be chemically or biochemically modified or may contain non-natural or derivatized nucleotide bases, as will be readily appreciated by those skilled in the art. Possible modifications include, for example, the addition of isotopic or non-isotopic labels, substitution of one or more of the naturally occurring nucleotide bases with an analog, internucleotide modifications such as uncharged linkages (e.g. methyl phosphonates, phosphoamidates, carbamates, etc.) or charged linkages (e.g. phosphorothioates, phosphorodithioates, etc.). Also included are synthetic molecules that mimic polynucleotides in their ability to bind to a designated sequence to form a stable hybrid. Such molecules are known in the art and include, for example, so-called peptide nucleic acids (PNAs) in which peptide linkages substitute for phosphate linkages in the backbone of the molecule. An oligonucleotide molecule according to the invention may be produced according to techniques well known in the art, such as by chemical synthesis or recombinant means.

The oligonucleotide molecules for inclusion into the kit are preferably single stranded and may correspond to the sense strand or the antisense strand of the relevant gene and to either allelic variant.

In a preferred embodiment, the kit comprises at least on oligonucleotide selected from:

5'-GGAAGGTGACCGAGAAAGAC-3' (SEQ ID NO:4) and
5'-GGAAGGTGACCGAGAAAGAT-3' (SEQ ID NO:5)

and at least one oligonucleotide selected from:

5'-CCAGCTCCCGGTCTTCC-3' (SEQ ID NO:17) and
5'-CCAGCTCCCGGTCTTCT-3' (SEQ ID NO:18)

and may additionally comprise oligonucleotides having the following sequences:

5'-TGGCCCAATGACACAGCCT-3' (SEQ ID NO:6) and
5'-AGAAGGTCGTGTCGGTCCAT-3' (SEQ ID NO:16)

The above-listed set of six oligonucleotides are suitable for performing PCR-SSP genotyping of the MAO 1460 C/T and the DBH 1368 A/G polymorphisms, as exemplified below.

The association which the present inventors have found between genetic variation in the dopamine β-hydroxylase gene and tobacco consumption identifies the dopamine β-hydroxylase enzyme as a novel target for pharmaceutical intervention in the development of treatments/therapies to assist in smoking cessation. In particular, inhibitors of dopamine β-hydroxylase are likely to ameliorate the withdrawal effects of nicotine. Accordingly, in a further aspect the invention also provides a method of ameliorating the symptoms associated with nicotine withdrawal in a human subject, which method comprises administering to a human subject in need thereof a therapeutically effective amount of a medicament comprising an inhibitor of dopamine β-hydroxylase.

Consistent with this aspect of the invention, there is also provided use of an inhibitor of dopamine β-hydroxylase as an aid to smoking cessation or to ameliorate the symptoms associated with nicotine withdrawal. The invention further provides use of an inhibitor of dopamine β-hydroxylase for the manufacture of a medicament for use as an aid to smoking cessation or to ameliorate the symptoms associated with nicotine withdrawal.

It is well documented that the cessation of cigarette smoking often results in the development of a nicotine withdrawal syndrome, as described by Benowitz, N L (1988) Pharmacologic aspects of cigarette smoking and nicotine addiction. *N. Engl. J. Med.*, 319, 1318-30.

Compounds which are inhibitors of dopamine β-hydroxylase activity could be identified using an in vitro assay of dopamine β-hydroxylase enzyme activity. The compound to be tested in such an assay may be of any chemical formula and may be one of known biological or pharmacological activity, a known compound without such activity or a novel molecule such as might be present in a combinatorial library of compounds.

The present invention will be further understood with reference to the following non-limiting Examples:

EXAMPLE 1

Identification of Genetic Variants Associated with Tobacco Consumption

Participants

Patients were selected from a cohort of people who responded to an invitation to see their general practitioner for a health check (ICRF, 1994; ICRF, 1995). From a total of 11,090 patients 8,109 attended for the check, 7,692 agreed to giving a blood sample and of these 1773 smoked cigarettes at the time of the interview. From these a sample of 234 smokers was picked using computer-generated random numbers. Blood was collected in EDTA and buffy coat lymphocytes were separated and stored at −80° C.

Genotyping

Polymorphisms were selected in monoamine oxidase A, monoamine oxidase B, catechol O-methyl transferase and dopamine β-hydroxylase on the basis that they could be typed using the polymerase chain reaction with sequence specific primers, using methods previously described for human leukocyte antigens (HLA) (Bunce, 1995). Reactions were developed to detect both the common allele and the variant allele. Each reaction mixture included control primers to detect a conserved sequence to eliminate the possibility of false negative results. Genomic DNA was isolated from samples and genotyped using the primers shown below:

Monoamine Oxidase A, Xp11.3, Exon 8 G941T (M68850)
  sense primer
    5'-CGTAATTAATGCGATCCCTCC-3' (SEQ ID NO: 1)
  antisense
    5'-GACAGCTCCCATTGGAAGC-3' (SEQ ID NO: 2)
    5'-GACAGCTCCCATTGGAAGA-3' (SEQ ID NO: 3)

Monoamine Oxidase A, Xp11.3, Exon 14 T1460C (M68856)
  sense primers
    5'-GGAAGGTGACCGAGAAAGAC-3' (SEQ ID NO: 4)
    5'-GGAAGGTGACCGAGAAAGAT-3' (SEQ ID NO: 5)
  antisense
    5'-TGGCCCAATGACACAGCCT-3' (SEQ ID NO: 6)

Monoamine Oxidase B, Xp11.3, Intron 13, G644A (Z29071)
  sense primer
    5'-CTGACAGTTCCTCTGATGTC-3' (SEQ ID NO: 7)
  antisense
    5'-CACACTGGCAAATAGCAAAAGC-3' (SEQ ID NO: 8)
    5'-CACACTGGCAAATAGCAAAAGT-3' (SEQ ID NO: 9)

Catechol O-methyl Transferase, 22q11.2, Exon 3, G11947A (Z26491), Val108Met
  sense primers
    5'-ATGGTGGATTTCGCTGGCG-3' (SEQ ID NO: 10)
    5'-ATGGTGGATTTCGCTGGCA-3' (SEQ ID NO: 11)
  antisense
    5'-GATGTCCTGGACGCTCC-3' (SEQ ID NO: 12)

Dopamine β-hydroxylase, 9q34, Exon 4, G910T (X13260), Ala304Ser
  sense primer
    5'-CCTGGGCCCTGGGTGCCA-3' (SEQ ID NO: 13)
  antisense primers
    5'-CCTGGACCCCCGAAGGC-3' (SEQ ID NO: 14)
    5'-CCTGGACCCCCGAAGGA-3' (SEQ ID NO: 15)

Dopamine β-hydroxylase, 9q34, Exon 8, G1368A (X13264)
  sense primer
    5'-AGAAGGTCGTGTCGGTCCAT-3' (SEQ ID NO: 16)
  antisense primers
    5'-CCAGCTCCCGGTCTTCC-3' (SEQ ID NO: 17)
    5'-CCAGCTCCCGGTCTTCT-3' (SEQ ID NO: 18)

Concentrations of the primers in the reaction mixture were adjusted so that all reactions were optimised for the same conditions. Buffers, PCR and gel electrophoresis conditions were as previously described (Bunce, 1995).

Sample Size and Statistical Analysis

A previous study on smokers in the OXCHECK cohort showed a mean (SD) of 14.9 (7.4) cigarettes smoked a day (Haldar et al submitted for publication). Assuming a standard deviation of 8.0 in each of two equal groups (with and without variant alleles) a study with 226 patients will have 80% power to detect a difference of three cigarettes a day (a=0.05). Pearson's coefficient was used to measure correlations between variables in the regression model. Stepwise linear regression was used to adjust differences in mean number of cigarettes smoked for potential confounders. In the analysis those having one or more variant alleles were grouped together and compared to those who were homozygous for the common allele. Differences in proportions with variant alleles across quartiles of cigarette consumption were compared using the $X^2$ test for linear trend.

Results

Clinical characteristics of the study group are shown in Table 1. DNA of sufficiently high quality for genotyping was extracted from 225 of the 234 samples taken from the randomly selected smokers. The numbers of cigarettes smoked for the alleles at each locus are shown in Table 2. The two monoamine oxidase A polymorphisms were strongly correlated (r=0.97, p<0.0001) in the study group. Alleles at the monoamine oxidase 941 locus were therefore omitted from regression analysis. The dopamine β-hydroxylase 910 and 1368 alleles were also significantly correlated although less strongly related (r=-0.183, p=0.003). These alleles were therefore analysed independently.

Linear regression was used to adjust for the effects of age, sex, social class and marital status on age at initiation of smoking. Women began smoking 2.4 (95% CI 0.07, 4.1) years earlier than men (p=0.006), however there was no effect of genetic polymorphisms on the age when participants started to smoke.

The effects that possession of variant alleles had on reported cigarette consumption were also examined. Smokers with one or more A alleles at the dopamine β-hydroxylase 1368 locus smoked significantly more cigarettes than those homozygous for the more common G allele. The mean (95% CI) difference after adjustment for age, sex and alcohol consumption was 3.3 (0.7, 5.7) cigarettes a day (p=0.009). In contrast, smokers with variant alleles (genotype CT or CC) at the monoamine oxidase 1460 locus smoked significantly fewer cigarettes. The adjusted mean difference was -3.2 (-5.4, -0.9) cigarettes a day (p=0.007).

The proportion of patients with one or more variant alleles by quartile of cigarette consumption is shown in Table 3. There was a significant trend for those who smoked more heavily to have one or more variant alleles at the dopamine β-hydroxylase 1368 locus. The relative risk for those smoking more than 20 a day compared to those smoking less than 10 a day was 2.32 (95% CI 1.1-5.0). A significant reversed trend was seen at the monoamine oxidase A 1460 locus with those smoking more than 20 a day being less likely to have variant alleles (genotype CT or CC), relative risk 0.31 (0.13-0.74).

The results of this study are likely to be generalisable because it was carried out on a cohort of smokers who responded to an invitation from their general practitioner to attend a health check. The response rate to the invitation was high implying that study participants are likely to be representative of the population who attend health centres in the United Kingdom. This is an advance on previous studies where recruitment often depended on response to a media advertisement (Lerman, 1997). Such studies may be biased by including substantial numbers of people whose tobacco dependence behaviour is atypical.

TABLE 1

Characteristics of the study population

| Characteristic | Study group |
| --- | --- |
| Age. (Years) | |
| mean (SD) | 50.1 (8.3) |
| median (range) | 49.0 (36 to 67) |
| Sex | |
| male N (%) | 100 (44%) |
| female N (%) | 125 (56%) |
| Number of cigarettes smoked each day | |
| mean (SD) | 16.7 (8.8) |
| median (range) | 15.0 (1 to 50) |
| Age at initiation of smoking (years) | |
| mean (SD) | 19.8 (6.5) |
| median (range) | 18.0 (5 to 53) |
| Alcohol consumed. (units a day) | |
| mean (SD) | 11.5 (20.3) |
| median (range) | 3.5 (0 to 145) |
| Socio-economic class N (%) | |
| Professional (I) | 6 (3%) |
| Managerial (II) | 30 (13%) |
| Clerical (IIIN) | 44 (19%) |
| Skilled manual (IIIM) | 54 (24%) |
| Semi skilled manual (IV) | 32 (14%) |
| Unskilled (V) | 8 (4%) |
| Housewife | 25 (11%) |
| Unclassified | 4 (2%) |
| No response | 22 (10%) |
| Marital status | |
| Married/living as married | 172 |
| Widowed | 14 |
| Divorced/separated | 23 |
| Single, never married | 13 |
| Unknown | 3 |

TABLE 2

Mean number of cigarettes smoked each day by genotype for dopamine metabolic enzymes

| Locus | Genotype | N (%) | Mean number of cigarettes smoked a day (95% CI) |
| --- | --- | --- | --- |
| Dopamine β-hydroxylase 910 | GG | 188 (84%) | 17.2 (16.0, 18.5) |
|  | GT | 37 (16%) | 14.2 (11.3, 17.1) |
| Dopamine β-hydroxylase 1368 | GG | 62 (28%) | 14.6 (12.5, 16.7) |
|  | GA or AA | 163 (72%) | 17.5 (16.1, 18.9) |
| Monoamine oxidase A 941 | TT | 138 (61%) | 17.6 (16.0, 19.1) |
|  | GT | 87 (39%) | 15.3 (13.7, 17.0) |
| Monoamine oxidase A 1460 | TT | 135 (60%) | 17.9 (16.3, 19.5) |
|  | CT or CC | 90 (40%) | 15.1 (13.4, 16.6) |
| Monoamine oxidase B | GG | 98 (44%) | 17.1 (15.3, 18.9) |

TABLE 2-continued

Mean number of cigarettes smoked each day by genotype for dopamine metabolic enzymes

| Locus | Genotype | N (%) | Mean number of cigarettes smoked a day (95% CI) |
|---|---|---|---|
| intron 13 | AG or AA | 127 (56%) | 16.4 (14.9, 17.9) |
| Catechol O-methyl | AA | 48 (21%) | 16.0 (13.6, 18.4) |
| transferase 1947 | AG or GG | 177 79%) | 16.1 (15.6, 18.3) |

TABLE 3

Proportion of patients with one or more variant allele by quartile of cigarette consumption Frequency of genotype by quartile of reported daily cigarette consumption N(%)[a]

| Locus | Genotype | 0-9 cigarettes | 10-14 cigarettes | 15-19 cigarettes | 20+ cigarettes | Significance[b] |
|---|---|---|---|---|---|---|
| Dopamine β-hydroxylase 910 | GT | 15 (21%) | 9 (17%) | 8 (13%) | 5 (13%) | 0.140 |
| Dopamine β-hydroxylase 1368 | AG or AA | 44 (63%) | 40 (77%) | 45 (71%) | 34 (85%) | 0.028 |
| Monoamine oxidase A 1460 | CT or CC | 34 (49%) | 19 (37%) | 28 (44%) | 9 (23%) | 0.033 |
| Monoamine oxidase B intron 13 | AG or AA | 42 (60%) | 30 (58%) | 33 (52%) | 22 (55%) | 0.447 |
| Catechol O-methyl transferase | AG or GG | 56 (80%) | 39 (75%) | 49 (78%) | 33 (83%) | 0.815 |

[a]Total Number of smokers in each category: 0-9 cigarettes a day, 70; 10-14 cigarettes a day, 52; 15-19 cigarettes a day, 63; 20+ cigarettes a day, 40.
[b]Chi square for linear trend

EXAMPLE 2

PATCH II Trial

Study Design

The PATCH II trial was carried out on a group of individuals receiving 'treatment' for smoking cessation in the form of a nicotine patch in order to evaluate the extent to which genetic variation influences smoking cessation in these individuals.

Methods

Genotyping of the monoamine oxidase A 1460 T/C and dopamine β-hydroxylase 1368 G/A polymorphisms was carried out as described in Example 1 above.

Results—Dopamine β-hydroxylase

TABLE 4

Smoking status in 1999:

| | | | Smoking status in 1999 | | |
|---|---|---|---|---|---|
| | | | Current smoker | Ex-smoker | Total |
| Dopamine β-hydroxylase | GG | Count | 22 | 13 | 35 |
| | | % within smoking status in 1999 | 33.3% | 52.0% | 38.5% |
| | GA or AA | Count | 44 | 12 | 56 |
| | | % within smoking status in 1999 | 66.6% | 48.0% | 61.5% |

TABLE 4-continued

Smoking status in 1999:

| | | | Smoking status in 1999 | | |
|---|---|---|---|---|---|
| | | | Current smoker | Ex-smoker | Total |
| Total | | Count | 66 | 25 | 91 |
| | | % within smoking status in 1999 | 100% | 100% | 100% |

TABLE 5

Risk estimate:

| | Value | 95% Confidence Interval | |
|---|---|---|---|
| | | Lower | Upper |
| Odds ratio for dopamine β-hydroxylase (GG/GA or AA) | 0.46 | 0.18 | 1.18 |
| N of valid cases | 91 | | | p = 0.147

The results of this study indicate that the dopamine β-hydroxylase A allele is more common in people who continue to smoke, whilst the G allele seems to be associated with successful cessation. About 60% of people with one or more A alleles continued to smoke, whereas only 40% of those with the GG genotype did so. This is consistent with the results from the OXCHECK patient cohort (Example 1) which supported an association between presence of one or more A alleles and high tobacco consumption.

EXAMPLE 3

Further Results from PATCH II Study

The following tables 6 and 7 show the numbers of patients given a nicotine patch who stopped smoking at one week on nicotine or placebo, broken down by genotype (results were similar at 12 weeks). The results indicate that nicotine replacement therapy is more effective in individuals carrying alleles known to be linked to smoking, i.e. the dopamine β-hydroxylase A allele and the DRD2 T allele.

TABLE 6

| | Patch | Placebo | |
|---|---|---|---|
| DBH: all with GA/AA | | | |
| Quit at one week | 104 (38.8) | 59 (23.1) | patch rate/placebo rate = 1.68 |
| Did not quit | 164 | 196 | patch rate/placebo rate = 15.7% |
| DBH: all with GG | | | |
| Quit at one week | 37 (37.4) | 34 (32.4) | patch rate/placebo rate = 1.15 |
| Did not quit | 62 | 71 | patch rate/placebo rate = 5.0% |

TABLE 7

| | Patch | Placebo | |
|---|---|---|---|
| DRD2: All with CT/TT | | | |
| Quit at one week | 68 (44.7) | 32 (22.1) | patch rate/placebo rate = 2.03 |
| Did not quit | 84 | 113 | patch rate/placebo rate = 22.7% |
| DRD2: All with CC | | | |
| Quit at one week | 73 (34.3) | 60 (28.0) | patch rate/placebo rate = 1.22 |
| Did not quit | 140 | 154 | patch rate/placebo rate = 6.2% |

REFERENCES

1. Callum C. The smoking epidemic, London, Health Education Authority, 1998.
2. ICRF. General Practice Research Group Effectiveness of a nicotine patch in helping people stop smoking: results of a randomised trial in general practice *BMJ* 1993;306(6888):1304-8.
3. Schneider N G, Olmstead R, Mody F V, et al. Efficacy of a nicotine nasal spray in smoking cessation: a placebo-controlled double-blind trial. *Addiction* 1995;90(12):1671-82.
4. Heath A C, Madden P A, Slutske W S, Martin N G Personality and the inheritance of smoking behaviour: a genetic perspective. *Behav Genet* 1995;25(2):103-17.
5. True W R, Heath A C, Scherrer J F, at al. Genetic and environmental contributions to smoking. *Addiction* 1997; 92(10):1277-87.
6. Heath A C, Cates R, Martin N G, et al. Genetic contribution to risk of smoking initiation; comparisons across birth cohorts and across cultures. *J Subst Abuse* 1993;5(3):221-46.
7. Clarke P B. Tobacco smoking, genes and dopamine *Lancet* 1998;352(9122):84-5.
8. Wicklegreen I. Teaching the brain to take drugs *Science* 1998;280(26 June):2045-2047.
9. Faraj B A, Davis D C, Camp V M, Mooney A J, 3rd, Holloway T, Barika G, Platelet monoamine oxidase activity in alcoholics, alcoholics with drug dependence, and cocaine addicts. *Alcohol Clin Exp Res* 1994;18(5):1114-20.
10. Fowler J S, Volkow N D, Wang G J, et al Neuropharmacological actions of cigarette smoke: brain monoamine oxidase B(MAO B) inhibition. *J Addict Dis* 1998;17(1):23-34.
11. Gabel S, Stadler J, Bjorn J, Shindledecker R, Homovanillic acid and dopamine-beta-hydroxylase in male youth; relationships with paternal substance abuse and antisocial behaviour. *Am J Drug Alcohol Abuse* 1995;21(3):363-78.
12. Vandenberg D J, Rodriguez L A Miller I T, Uhl G R, Lachman H M, High-activity catechol-O-methyltransferase allele is more prevalent in polysubstance abusers. *Am J Med Genet* 1997;74(4):439-42.
13. ICRF. OXCHECK Study Group. Effectiveness of health checks conducted by nurses in primary care results of the OXCHECK study after one year. *BMJ* 1994;308(6924):308-12.
14. ICRF. OXCHECK Study Group. Effectiveness of health checks conducted by nurses in primary care: final results of the OXCHECK study. *BMJ* 1995;310(6987):1099-104.
15. Bunce M, O'Neill C M, Barnardo M C, et al Phototyping: comprehensive DNA typing for HLA-A, B, C, DRB1, DRB3, DRB4, DRB5 & DQB1 by PCR with 144 primer mixes utilizing sequence-specific primers (PCR-SSP) *Tissue Antigens* 1995;46(5):355-67.
16. Lerman C, Shields P G, Main D, et al. Lack of association of tyrosine hydroxylase genetic polymorphism with cigarette smoking *Pharmacogenetics* 1997;7(6):521-4.
17. Bunce M, Young N T, Welsh K I. Molecular HLA typing the brave new world, *Transplantation* 1997;64(11):1505-13.
18. Bell J. The new genetics in clinical practice *BMJ* 1998; 316(14 February):618-620.
19. Rossing M A. Genetic influences on smoking: candidate genes. *Environ Health Perspect* 1998;106(5):231-8
20. Comings D E, Gade R, Wu S, et al. Studies of the potential role of the dopamine D1 receptor gene in addictive behaviours. *Mol Psychiatry* 1997;2(1):44-56.
21. Comings D E, Ferry L, Bradshaw-Robinson S, Burchette R, Chiu C. Muhleman D. The dopamine D2 receptor (DRD2) gene: a genetic risk factor in smoking. *Pharmacogenetics* 1996;6(1):73-9
22. Noble E P, St. Jeor S T, Ritchie T, et al. D2 dopamine receptor gene and cigarette smoking: a reward gene? *Med Hypotheses* 1994;42(4):257-60.
23. Lerman C, Caporaso N E, Audrian J. et al. Evidence suggesting the role of specific genetic factors in cigarette smoking. *Health Psychol* 1999;18(1):14-20.
24. Sabol S Z, Nelson M L, Fisher C, et al. A genetic association for cigarette smoking behaviour. *Health Psychol* 1999;18(1):7-13.
25. Shields P G, Lerman C. Audrain J. et al. Dopamine D4 receptors and the risk of cigarette smoking in African-Americans and Caucasians. *Cancer Epidemiol Biomarkers Prev* 1998;7(6):453-8.
26. Garcia-Closas M, Caporaso N, Kelsey K, Christiani D, Association between CYP1A1 polymorphism and smoking in a control population: implications for the study of genetic factors on cancer risk. *Proceedings of the American Association for Cancer Research* 1997;38(March 1997):211.
27. Cholerton S, Arpanahi A, McCracken N, et al. Poor metabolisers of nicotine and CYP2D6 polymorphism *Lancet* 1994;343(8888):62-3.
28. Boustead C, Taber H, Idle J R, Cholerton S. CYP2D6 genotype and smoking behaviour in cigarette smokers. *Pharmacogenetics* 1997;7(5):411-4.
29. Cubells J F, van Kammen D P, Kelley M E, et al. Dopamine beta-hydroxylase: two polymorphisms in linkage disequilibrium at the structural gene DBH associate with biochemical phenotypic variation *Hum Genet* 1998;102(5):533-40.

30. Sabol S Z, Hu S, Hamer D. A functional polymorphism in the monoamine oxidase A gene promoter. *Hum Genet* 1998;103(3):273-9.
31. Blum K, Sheridan P J, Wood R C. Braverman E R. Chen T J, Comings D E. Dopamine D2 receptor gene variants: association and linkage studies in impulsive-addictive-compulsive behaviour. *Pharmacogenetics* 1995;543 . . . -41.
32. Hurt R D, Sachs D P, Gover E D, et al. A comparison of sustained-release bupropion and placebo for smoking cessation. *N Engl J Med* 1997;337(17):1195-202.
33. Jorenby D E, Leischow S J, Nides M A, et al. A controlled trial of sustained-release bupropion, a nicotine patch, or both for smoking cessation. *N Engl J Med* 1999;340(9): 685-91.
34. van der Sande M A, Bailey R, Faal H, et al. Nationwide prevalence study of hypertension and related non-communicable diseases in The Gambia, *Trop Med Int Health* 1997; 2(11):1039-48.
35. Mackay J, Crofton J. Tobacco and the developing world. *Br Med Bull* 1996;52(1):206-21.
36. Pianezza M L, Sellers E M, Tyndale R F. Nicotine metabolism defect reduces smoking. *Nature* 1998;393:750.
37. Sellers E M. Pharmacogenetics and ethnoracial differences in smoking. *JAMA* 1998;280(2):179-80.
38. Caporaso N E, Lerman C, Main D, Audrain J, Boyd N R, Bowman E, Shields P. The genetics of smoking: the dopamine receptor transporter (DAT) polymrophisms in a smoking cessation study (absract). *Proc. Am. Assoc. Cancer Res.* 1997;38:168-169.

| Abbreviations | |
|---|---|
| MAO A | Human monoamine oxidase A gene |
| DBH | Human dopamine β-hydroxylase gene |
| DAT 1 | Human dopamine transporter gene |
| CYP2AG | Human coumarin 7-hydroxylase gene |
| 5-HTT | Human 5-hydroxytryptamine (serotonin) transporter gene |
| TH | Human tyrosine hydroxylase gene |
| CYP2D6 | Human debrisoquine-4-hydroxylase gene |
| RFLP | Restriction fragment length polymorphism |
| VNTR | Variable number tandem repeat |
| SNP | Single nucleotide polymorphism |

The invention claimed is:

1. A method for predicting a response of a human subject to a nicotine replacement treatment designed to assist smoking cessation, the method comprising screening the genome of the human subject for the presence and genotype of dopamine β-hydroxylase 1368 alleles and dopamine D2 receptor Taq I RFLP alleles, wherein the presence of a dopamine β-hydroxylase 1368 A allele and a dopamine D2 receptor Taq I RFLP T allele in the genome of the human subject is predictive of an effective response to the nicotine replacement treatment in the subject.

2. The method of claim 1, wherein the presence of at least one dopamine D2 receptor Taq I RFLP T allele and at least one dopamine β-hydroxylase 1368 A allele indicates that the treatment will be more effective in the subject than in a subject homozygous for a dopamine D2 receptor Taq I RFLP C allele and homozygous for a dopamine β-hydroxylase 1368 G allele.

3. The method of claim 1, wherein screening for the dopamine β-hydroxylase 1368 alleles comprises amplifying genomic DNA of the subject using the forward primer sequence set forth as SEQ ID NO 16 in conjunction with the reverse primer sequence set forth as SEQ ID NO 17 or the reverse primer sequence set forth as SEQ ID NO 18.

4. A method for predicting a response of a human subject to a nicotine replacement treatment designed to assist smoking cessation, the method comprising screening for the presence in the genome of the human subject of SEQ ID NO:18 or SEQ ID NO:17, which identify the dopamine β-hydroxylase 1368 alleles, and screening for the presence of the dopamine D2 receptor Taq I RFLP alleles, wherein the presence of SEQ ID NO:18, which comprises the dopamine β-hydroxylase 1368 A allele, and the presence of a T allele of the dopamine D2 receptor Taq I RFLP is predictive of an effective response to the nicotine replacement treatment in the subject.

5. The method of claim 4, wherein the presence of at least one T allele of the dopamine D2 receptor Taq I RFLP and at least one dopamine β-hydroxylase 1368 A allele indicates that the treatment will be more effective in the subject than in a subject homozygous for a C allele of the dopamine D2 receptor Taq I RFLP and a dopamine β-hydroxylase 1368 G allele.

6. A method for predicting a response of a human subject to a nicotine replacement treatment designed to assist smoking cessation, the method comprising obtaining a sample comprising genomic DNA of the subject and screening the sample for the presence and genotype of dopamine β-hydroxylase 1368 alleles and dopamine D2 receptor Taq I RFLP alleles, wherein the presence of a dopamine β-hydroxylase 1368 A allele and a dopamine D2 receptor Taq I RFLP T allele in the genomic DNA of the subject is predictive of an effective response to the nicotine replacement treatment in the subject.

7. The method of claim 6, wherein the presence of at least one dopamine D2 receptor Taq I RFLP T allele and at least one dopamine β-hydroxylase 1368 A allele in the sample from the subject indicates that the treatment will be more effective in the subject than in a subject homozygous for a dopamine D2 receptor Taq I RFLP C allele and homozygous for a dopamine β-hydroxylase 1368 G allele.

8. The method of claim 6, wherein screening for the dopamine β-hydroxylase 1368 A allele comprises amplifying genomic DNA of the subject using the forward primer sequence set forth as SEQ ID NO 16 in conjunction with the reverse primer sequence set forth as SEQ ID NO 17 or the reverse primer sequence set forth as SEQ ID NO 18.

* * * * *

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
cgtaattaat gcgatccctc c                                               21

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
gacagctccc attggaagc                                                  19

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 3
gacagctccc attggaaga                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
```
ggaaggtgac cgagaaagac                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
ggaaggtgac cgagaaagat                          20

<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 6
tggcccaatg acacagcct                           19

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ctgacagttc ctctgatgtc                          20

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
cacactggca aatagcaaaa gc                       22

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
cacactggca aatagcaaaa gt                       22

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 10
atggtggatt tcgctggcg                           19

<210> SEQ ID NO 11
<211> LENGTH: 19
<212> TYPE: DNA

```
<213> ORGANISM: Artificial Sequence
<220> FEATURE:
<223> OTHER INFORMATION: Synthetic Oligonucleotide

<400> SEQUENCE: 11
atggtggatt tcgctggca                                                    19

<210> SEQ ID NO 12
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 12
gatgtcctgg acgctcc                                                      17

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
cctgggccct gggtgcca                                                     18

<210> SEQ ID NO 14
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 14
cctggacccc cgaaggc                                                      17

<210> SEQ ID NO 15
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 15
cctggacccc cgaagga                                                      17

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
agaaggtcgt gtcggtccat                                                   20

<210> SEQ ID NO 17
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 17
ccagctcccg gtcttcc                                                      17
```

```
<210> SEQ ID NO 18
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 18
ccagctcccg gtcttct                                                17
```